(12) United States Patent
Shim et al.

(10) Patent No.: US 9,890,947 B2
(45) Date of Patent: Feb. 13, 2018

(54) PREDICTION METHOD FOR CORROSION RATE OF STEAM GENERATOR TUBE USING EDDY CURRENT TESTING

(71) Applicant: KOREA ATOMIC ENERGY RESEARCH INSTITUTE, Daejeon (KR)

(72) Inventors: Hee Sang Shim, Daejeon (KR); Myung-sik Choi, Daejeon (KR); Do-Haeng Hur, Daejeon (KR); Deok-Hyun Lee, Seoul (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 207 days.

(21) Appl. No.: 14/711,929

(22) Filed: May 14, 2015

(65) Prior Publication Data

US 2016/0069788 A1    Mar. 10, 2016

(30) Foreign Application Priority Data

Sep. 5, 2014    (KR) .................. 10-2014-0119092

(51) Int. Cl.
*G01N 17/04* (2006.01)
*F22B 37/00* (2006.01)
*G01N 27/90* (2006.01)
*G01N 17/00* (2006.01)

(52) U.S. Cl.
CPC ......... *F22B 37/002* (2013.01); *G01N 17/008* (2013.01); *G01N 27/9046* (2013.01)

(58) Field of Classification Search
None
See application file for complete search history.

(56) References Cited

U.S. PATENT DOCUMENTS

| 4,763,274 A * | 8/1988 | Junker | G01N 27/9093 |
| | | | 324/220 |
| 2002/0153883 A1 * | 10/2002 | Hur | G01N 27/9013 |
| | | | 324/220 |

(Continued)

FOREIGN PATENT DOCUMENTS

| JP | 2000-275165 | 10/2000 |
| JP | 2012-159471 | 8/2012 |
| KR | 10-1083215 B1 | 11/2011 |

*Primary Examiner* — Jermele M Hollington
*Assistant Examiner* — Suresh K Rajaputra
(74) *Attorney, Agent, or Firm* — Sheridan Ross P.C.

(57) ABSTRACT

Disclosed herein is a method including: performing eddy current testing on a steam generator tube material by using a motorized rotating pancake coil (MRPC) probe, evaluating a test signal measured using the eddy current testing, and predicting the corrosion rate of the steam generator tube material from a noise value in the MRPC inspection signal of the steam generator tube obtained from the evaluating. When the prediction method of a corrosion rate of a steam generator tube according to the present invention is used, the steam generator tube material which has low corrosion rate can be selected at the material selecting step because the corrosion rate can be predicted and the criterions on the corrosion rate of the steam generator tube can be established as the requirements through an eddy current MRPC noise inspection of the steam generator tube material.

8 Claims, 5 Drawing Sheets

(56) References Cited

U.S. PATENT DOCUMENTS

2010/0301851 A1* 12/2010 Park .................... B24B 49/105
 324/240
2011/0054813 A1* 3/2011 Moreau .............. G01N 27/9006
 702/59

* cited by examiner

PREDICTION METHOD FOR CORROSION RATE OF STEAM GENERATOR TUBE USING EDDY CURRENT TESTING

This patent application claims the benefit of priority under 35 U.S.C. §119 from Korean Patent Application No. 10-2014-0119092 filed Sep. 5, 2014, the contents of which are incorporated herein by reference.

BACKGROUND OF THE INVENTION

1. Field of the Invention

The present disclosure relates to a method of predicting a corrosion rate of a steam generator tube using eddy current test, and more particularly, to a method of performing eddy current test using a motorized rotating pancake coil (MRPC) and predicting a corrosion rate of a steam generator tube from an MRPC noise value.

2. Description of the Related Art

The integrity of nuclear power plants is influenced by corrosion damages and mechanical erosions of their consisting materials in coolant system. Particularly, steam generator tube, which occupies about 70% of primary surface area and is exposed simultaneously to primary and secondary coolants, is a crucial structural component to secure the integrity of nuclear power plant. The corrosion release of metal ions or corrosion products from steam generator tube which causes the increase of radiation dose in primary coolant system or axial offset anomaly (AOA) becomes more important because the corrosion damages of steam generator tubes such as stress corrosion cracking and intergranular attack are still reported since the steam generator tubing material is replaced from Alloy 600 to Alloy 690. The corrosion release rate can be predicted indirectly through in-situ monitoring of dose amount for $^{58}$Co and $^{60}$Co as major radiation sources during operation of nuclear power plant. Then, it has been reported that corrosion release properties of the steam generator tube are influenced by various factors including material intrinsic properties such as its chemical composition or surface property and manufacturing methods. Therefore, to employ the steam generator tubes having excellent corrosion release resistance is very important from manufacturing step prior to any others and the establishment of an innovative prediction method for corrosion release properties at a selection step of materials or a manufacturing step of steam generator is needed.

The eddy current test (ECT) is typically used for evaluating in-service integrity of the steam generator tube. The eddy current signal is typically influenced by manufacturing quality of the steam generator tube, corrosion products and foreign objects deposited on the steam generator tube surface, or its adjacent structures. Thus, to reduce the influence factors on the eddy current signal is very important to improve a probability of detection and it indicates that the manufacturing quality of steam generator tube becomes more significant. However, a bobbin signal-to-noise (S/N) ratio is only required currently at the manufacturing step of the steam generator for improving the probability of detection during in-service inspection. According to the practical results, it has been reported that the radiation doses of $^{58}$CO and $^{60}$CO were varied by producing factors of steam generator tubes such as manufacturing periods or type of process, although the steam generator tube satisfies the requirement for the bobbin S/N ratio. In addition, criterion on the corrosion release property is not yet established as a requirement and there is no method capable of predicting them in advance.

Meanwhile, as an existing technology related to the eddy current testing of the steam generator tube, Korean patent No. 10-1083215 discloses an eddy current testing method using an MRPC probe for inner diameter circumferential crack of a steam generator tube. In detail, it discloses the ECT method using an MRPC probe for inner diameter circumferential crack of the steam generator tube including: (a) obtaining the eddy current signals with varying frequencies of the MRPC inspection on the steam generator tubes; (b) analyzing signals obtained through the ECT under different frequencies and inspecting the inner diameter circumferential crack; (c) drawing a calibration curve for the inner diameter circumferential crack and selecting the eddy current signal at any one frequency among the ECT signals at several frequencies; (d) measuring a depth from a starting point to a ending point of the crack with predetermined interval; and (e) calculating a percent degraded area (PDA) considering a crack shape and length. However, the prediction of corrosion and release properties becomes more significant than the measurement of its corrosion damages such as stress corrosion cracking (SCC) because they are still reported for Alloy 690 dislike Alloy 600 as a typical steam generator tube material.

Therefore, the inventors found that MRPC noise signals have a relationship with the corrosion rate of the steam generator tube when they were performing the study on the prediction method for corrosion and release properties of steam generator tube and then completed the present invention possible to predict the corrosion and release properties of steam generator tubes at the component selection step.

SUMMARY OF THE INVENTION

Embodiments of the present invention are directed to provide a method of predicting corrosion rate of a steam generator tube material using an eddy current test (ECT).

According to an aspect of the present invention, there is provided a method of predicting a corrosion rate of a steam generator tube using the ECT. This method includes: performing the ECT on a steam generator tube using a motorized rotating pancake coil (MRPC) probe; evaluating the test signals obtained by the ECT; and predicting the corrosion rate of the steam generator tube from a MRPC noise value of the steam generator tube referred to the correlation between corrosion rate and MRPC noise.

The present invention makes possible to choosing the qualitative steam generator tube with low corrosion rate at the material selection step because the corrosion rate of steam generator tube in a primary coolant condition can be predicted through the MRPC noise inspection and the criterions for the corrosion rate of steam generator tube can be established.

Furthermore, it is possible that the integrity of nuclear reactor will be innovatively improved because the corrosion deposits on fuel cladding surface can be reduced as well as the radiation dose in the primary coolant system of nuclear power plant by manufacturing the steam generator with the steam generator tube having excellent corrosion resistance.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Features and advantages of the present invention will be more clearly understood by the following detailed description of the present preferred embodiments with respect to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, specific embodiments of the present invention will be described in detail with respect to the accompanying drawings.

The present invention provides a method of predicting a corrosion rate of a steam generator tube using the ECT, which includes:

performing the ECT on a steam generator tube material using a Motorized Rotating Pancake Coil (MRPC) probe (operation 1);

evaluating the signals obtained by the ECT (operation 2); and predicting a corrosion rate of a steam generator tube from its MRPC noise value where it is obtained by the evaluation (operation 3).

Figure 1:
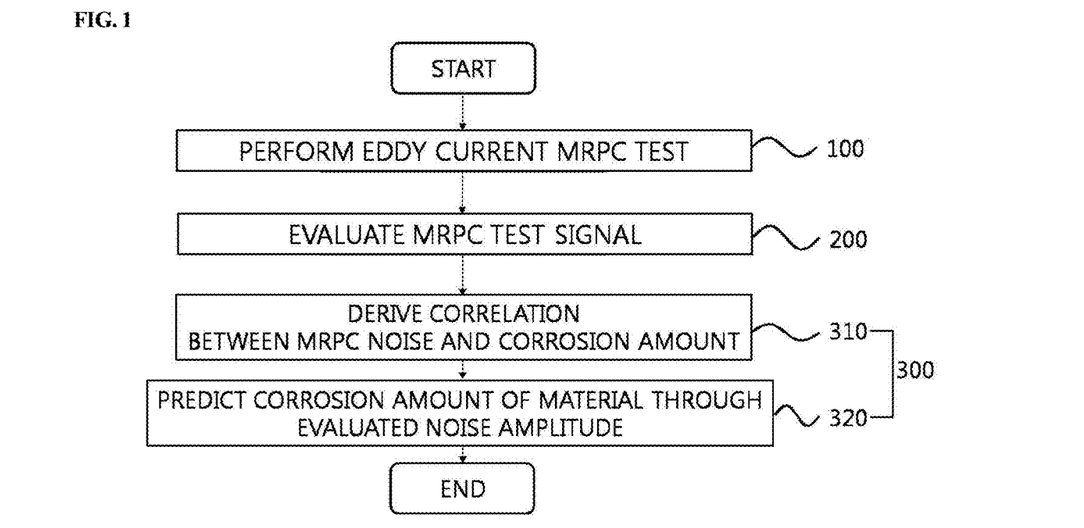
FIG. 1 illustrates an exemplary schematic diagram of a method of predicting a corrosion rate of a steam generator tube using the ECT according to the present invention.

At this point, an exemplary embodiment of the present invention is illustrated in FIG. 1, and, hereinafter, a method is described in detail which predicts a corrosion rate of a steam generator tube using the ECT.

Typically, the bobbin S/N ratio is only employed as a requirement in the selecting step of the steam generator tube, which affects to detectability of corrosion damages during in-service inspection. However, the eddy current MRPC inspection is not involved as a requirement in the material selection step and is used for detailed inspection of corrosion damages such as stress corrosion cracking, when they are detected by the bobbin inspection.

In the present invention, which is different from a related art, the correlation between the eddy current MRPC noise and the corrosion rate may be derived by performing the MRPC probe inspection at the material selection step and sequentially quantifying the corrosion rate using a primary simulation loop of a nuclear power plant. Accordingly, the corrosion rate of the steam generator tube, which can occur during practical operation of the nuclear power plant, may be predicted, and, through this, criterions for the corrosion and release properties of the steam generator tube may be made as the requirements.

At this point, the corrosion rate prediction can be performed at a selection step of the steam generator tube material. In a related art, the bobbin signal-to-noise ratio is only employed as the requirement at the selection step of the steam generator tube material, which affects the detectability of corrosion damages during the in-service inspection. In the present invention, which is different from the related art, the eddy current MRPC inspection is performed at the selection step of the steam generator tube material and the corrosion rate can be predicted through it.

In the method of predicting a corrosion rate of a steam generator tube, operation 1 is an operation of performing the ECT on the steam generator tube using the MRPC probe (100). At this point, the eddy current MRPC inspection in the operation 1 may use an MRPC +Point coil or a pancake coil, and, in particular, a +Point magnetic-bias detachable probe may be used. However, the present invention is not limited hereto and a probe having the same function as them may be used. A test frequency at this point may be employed in a frequency range from about 100 to 1000 kHz.

Operation 2 in the predicting method of the corrosion rate of the steam generator tube according to the present invention is an evaluating step of the MRPC signal obtained by the ECT (200). Noise signal amplitude may be derived from the MRPC inspection signal obtained at operation 1 and used for the corrosion rate prediction.

As an exemplary method of deriving the noise signal amplitude from the MRPC inspection signal, the eddy current MRPC signal may be calibrated by using a signal from an axial through-wall notch standard tube having a 0.375 inch length, produced using electric discharge machine (EDM) and a relative noise signal amplitude may be evaluated in comparison to an amplitude of a 100% axial defect signal along with examining a long strip chart, an X-Y display and a C-scan signal for a test target steam generator tube, after a signal phase is adjusted to 30 degrees and the signal amplitude to 20V with respect to 100% axial defects of a calibration standard tube. Then, the amplitude of the noise signal may be evaluated from the C-scan signal which may consist of a vertical component and a horizontal component.

In the method of predicting the corrosion rate of the steam generator tube according to the present invention, operation 3 is an operation of predicting the corrosion rate of the steam generator tube from a MRPC noise value of the steam generator tube, which is obtained by the evaluation (300). In operation 3, the corrosion rate of the steam generator tube, which can be occurred during the practical operation of the nuclear power plant, can be predicted by the correlation derived in advance from the MRPC noise value.

The corrosion rate prediction may be performed through the correlation between the noise value of the pre-measured MRPC noise signal and the corrosion rate.

In detail, the corrosion rate of a specific steam generator tube material may be predicted by substituting the MRPC noise value measured from the specific steam generator tube into a pre-derived correlation between a MRPC noise value and a corrosion rate (320).

The correlation between the MRPC noise value and the corrosion rate may be derived from operations including (310):

measuring a noise value of an eddy current MRPC inspection signal of a steam generator tube (operation a);

measuring a corrosion rate of the steam generator tube in operation a using a primary simulation loop of a nuclear power plant (operation b); and deriving a correlation between the MRPC noise measured in operation a and the corrosion rate measured in operation b (operation c).

In the method of deriving the correlation between the MRPC noise value and the corrosion rate value according to the present invention, operation a is an operation of measuring the MRPC noise value of the steam generator tube.

The eddy current MRPC inspection signal may be measured by using an MRPC +Point coil or a pancake coil, and, in particular, by using the +Point magnetic-bias detachable probe. However, the present invention is not limited hereto and a probe having the same function with them may be used. Then, the test frequency may be used in the range from about 100 to 1000 kHz.

The noise value of the eddy current MRPC inspection signal may be amplitude of a relative noise signal comparing with that of the 100% axial defect signal of a standard tube for signal calibration. In detail, as an exemplary method of deriving the noise value from the MRPC inspection signal, the eddy current MRPC signal may be calibrated by using a signal from an standard tube having an EDM notch of 0.375 inch length, and a relative noise signal amplitude may be evaluated in comparison to an amplitude of a 100% axial defect signal along with examining a long strip chart, an X-Y display and a C-scan signal for a test target steam generator tube signal, after a signal phase is adjusted to 30 degrees and the signal amplitude to 20V with respect to 100% axial defects of a calibration standard tube. Then, the amplitude of the noise signal may be evaluated from the C-scan signal which may consist of a vertical component and a horizontal component.

In the method of deriving the correlation between the noise value of the MRPC inspection signal and the corrosion rate according to the present invention, operation b is an operation of quantifying the corrosion rate of the steam generator tube in operation a using a simulation loop of a nuclear power plant.

In order to predict the corrosion rate of the steam generator tube in the practical operation of the nuclear power plant, the corrosion rate of the steam generator tube is quantified using the simulation loop in operation b and then, the correlation may be derived between the MRPC noise value and the corrosion rate in follow-up operations.

At this point, the nuclear power plant simulation loop may be a simulation equipment of a primary system or a secondary system. Integrity of a nuclear power plant is affected by corrosive damage, mechanical wear, etc., during the in-service operation. In particular, a steam generator tube, which occupies about 70% of a surface area of the primary coolant system and is exposed to both the primary and secondary systems, is a very important consisting material for securing integrity of the nuclear power plant.

In the present invention, the corrosion rate may be specified through the primary simulation loop of the nuclear power plant and then compared with measured MRPC noise value in order to predict the corrosion rate of the steam generator tube in the nuclear power plant.

In the method of deriving the correlation between the MRPC noise value and the corrosion rate according to the present invention, operation c is an operation of deriving the correlation between the MRPC noise value measured in operation a and the corrosion rate measured in operation b.

In operation c, the MRPC noise value is compared with the corrosion rate, and the correlation may be derived through a calibration curve so that the corrosion rate may be predicted from the noise value of the MRPC inspection signal.

At this point, the correlation derived in operation c may be that the MRPC noise value is proportion to the corrosion rate of the steam generator tube under the primary coolant system condition. For example, the corrosion rate may be increased approximately proportionally as the noise value of the MRPC inspection signal increases.

Furthermore, the present invention provides a method of selecting a steam generator tube material, which includes:

performing an eddy current MRPC inspection on a steam generator tube (operation 1);

evaluating a signal from the MRPC inspection performed in operation 1 (operation 2); and evaluating the steam generator tube material through a noise amplitude of the MRPC inspection signal evaluated in operation 2 (operation 3).

Hereinafter, the method of selecting the steam generator tube material according to the present invention is described in detail for each operation.

In the method of selecting the steam generator tube material according to the present invention, operation 1 is an operation of performing the eddy current MRPC inspection on the steam generator tube. In the present invention, the eddy current MRPC inspection is performed in the material selection step and the corrosion rate of the steam generator tube material may be predicted, which can occur in the practical operation of the nuclear power plant, from the noise value obtained by the eddy current MRPC inspection.

At this point, the eddy current MRPC inspection in the operation 1 may use a motorized rotating +Point coil or a pancake coil. In particular, a +Point magnetic-bias detachable probe may be used. However, the present invention is not limited hereto and a probe having the same function with them may be used. A test frequency at this point may be under a frequency condition from about 100 to 1000 kHz.

The steam generator tube material in operation 1 may be Alloy 690.

In the method of selecting the steam generator tube material according to the present invention, operation 2 may be an operation of evaluating a noise signal from the MRPC inspection performed in operation 1. The noise signal amplitude may be derived from the MRPC inspection signal obtained at operation 1 and the steam generator tube satisfying evaluation criterions may be selected from following operations.

As an exemplary method of deriving the noise amplitude from the MRPC signal, the MRPC signal may be calibrated by using a signal of a standard tube having an EDM notch of a 0.375 inch length, and a relative noise amplitude may be evaluated in comparison to an amplitude of 100% axial defect signal with examining a long strip chart, an X-Y display and a C-scan signal for a test target steam generator tube, after a signal is adjusted to a phase angle of 30° and the signal amplitude to 20V with respect to 100% axial defect of a calibration standard tube. At this point, the C-scan signal may be distinguished into a vertical component and a horizontal component and used to evaluate the amplitude of the noise signal.

In the method of selecting the steam generator tube according to the present invention, operation 3 is an operation of evaluating the steam generator tube material from the noise amplitude of the MRPC signal evaluated in operation 2. In operation 3, the corrosion rate of the steam generator tube, which can occur in the practical operation of the nuclear power plant, may be predicted through a pre-derived correlation, and, through this, a steam generator tube satisfying evaluation criterions may be selected in the operation of selecting the steam generator tube.

In addition, the present invention provides an apparatus for predicting a corrosion rate of a steam generator tube using an ECT including:

an ECT unit performing the eddy current test on a steam generator tube material using an MRPC probe;

a signal evaluation unit evaluating a test signal obtained by the ECT; and a corrosion rate prediction unit predicting the corrosion rate of a steam generator tube material from a noise value of the MRPC test signal of the steam generator tube, which is obtained in the signal evaluation unit.

Hereinafter, the apparatus for predicting a corrosion rate of a steam generator tube using an ECT is described in detail.

According to the apparatus for predicting a corrosion rate of a steam generator tube using an ECT, the ECT unit may perform the ECT inspection on an employed steam generator tube material using an MRPC probe and obtain a test signal.

In the eddy current test, a motorized +Point coil or a pancake coil may be used. In particular, +Point Magnetic-Bias Detachable probe may be used, but is not limited to them, and a probe having the same function may be used. A test frequency at this point may be under a frequency condition from about 100 to about 1000 kHz.

According to the apparatus for predicting a corrosion rate of a steam generator tube using an ECT, the signal evaluation unit evaluates a test signal obtained by the ECT unit. Noise signal amplitude may be derived from the MRPC test signal to be used for corrosion rate prediction.

As an example of a method of deriving the noise signal amplitude from the MRPC test signal, the eddy current MRPC signal may be calibrated by using a signal from an axial through-wall electric discharge machine (EDM) notch standard tube whose length is 0.375 inches. A relative noise signal amplitude may be evaluated in comparison to an amplitude of a 100% axial defect signal along with examining a long strip chart, an X-Y display and a C-scan signal for a test target steam generator tube signal, after a signal phase is adjusted to 30 degrees and the signal amplitude to 20V with respect to 100% axial defects of a calibration standard tube. Then, the amplitude of the noise signal may be evaluated from the C-scan signal which may consist of a vertical component and a horizontal component.

According to the apparatus for predicting a corrosion rate of a steam generator tube using an ECT, the corrosion rate prediction unit may predict a corrosion rate of the steam generator tube material from a noise value of the MRPC test signal, which is obtained from the signal evaluation unit. The corrosion rate of the steam generator tube material, which is experienced in an operation condition of a nuclear power plant, may be predicted from the noise value of the MRPC test signal through correlation derived in advance.

The corrosion rate predicting unit may predict the corrosion rate with the noise value of measured MRPC signal from the correlation between the MRPC noise and the corrosion rate.

In detail, the corrosion rate of the specific steam generator tube material may be predicted by substituting the noise value of the MRPC signal measured from a steam generator tube material to the correlation between the MRPC noise and the corrosion rate derived in advance.

The corrosion rate predicting unit may further include a correlation deriving unit capable of deriving the correlation between the MRPC noise and the corrosion rate and may predict the corrosion rate of the steam generator tube from the noise value of the signal evaluation unit using a calibration curve obtained by the correlation deriving unit.

Hereinafter, the present invention is described in detail through experimental examples. However, the below experimental examples are only for explaining the present invention and the present invention is not limited to them.

<Experimental example> prediction of a corrosion rate of a specific steam generator tube from correlation between an MRPC noise value and the corrosion rate Below experiment was performed for predicting a corrosion rate of a specific steam generator tube from a correlation between an MRPC noise value and a corrosion rate Operation 1: An MRPC inspection was performed for a commercially available steam generator tube of Alloy 690 having at least 50 cm length using a ZETEC MRPC +Point Magnetic-Bias Detachable probe including P115A Unshielded Primary Test Coil, PP11A +Point Coil, and SP080B Shielded High Frequency Pancake Coil. At this point, test frequencies were compared and collected at 300 kHz as a detection frequency of +Point coil. Signal collection was performed by using ZETEC EddynetAN Analysis equipment and MIZ-70 Data Acquisition software.

Operation 2: The MRPC signals for three steam generator tube specimens examined in operation 1 were calibrated through an EDM notch standard tube having a length of 0.375 inch. At this point, for the 100% axial defect of the EDM notch standard tube, a signal phase was adjusted to 30 degrees and signal amplitude is adjusted to 20V. Relative noise amplitude in comparison to 100% defect signal amplitude of a standard tube was measured with examining a Long strip chart, an X-Y display and a C-scan signal for the test target steam generator tube.

Then, the examined steam generator tube specimen was cut with 50 mm length and it was cleaned using an ultrasonicator for 15 minutes in acetone, methanol, ethanol, and deionized water, respectively, and dried with nitrogen gas. Finally the specimen was dried for 15 minutes in an oven of 70° C. to remove the moisture.

Operation 3: Corrosion test was performed for each steam generator tube specimen in operation 2 using a simulated primary loop of the nuclear power plant after weighing them. Corrosion and release tests were carried out in the simulated primary coolant including 2 ppm Li and 1200 ppm B at 330° C. and 150 bar with maintaining dissolved hydrogen and dissolved oxygen to 35 cc/kg $H_2O$ and less than 10 ppb, respectively. In addition, the corrosion rate was quantified through a chemical descaling process for the surface corrosion products after corrosion and release test. Furthermore, a quantified correlation was derived between the MRPC noise value evaluated in operation 2 and the corrosion rate obtained under a high temperature/high pressure primary condition examined through this experimental result.

Operation 4: the corrosion rate of the steam generator tube having the specific MRPC noise was predicted from the calibration curve derived in operation 3.

Hereinafter, the experimental result performed through the experimental examples is described in detail.

Figure 2:
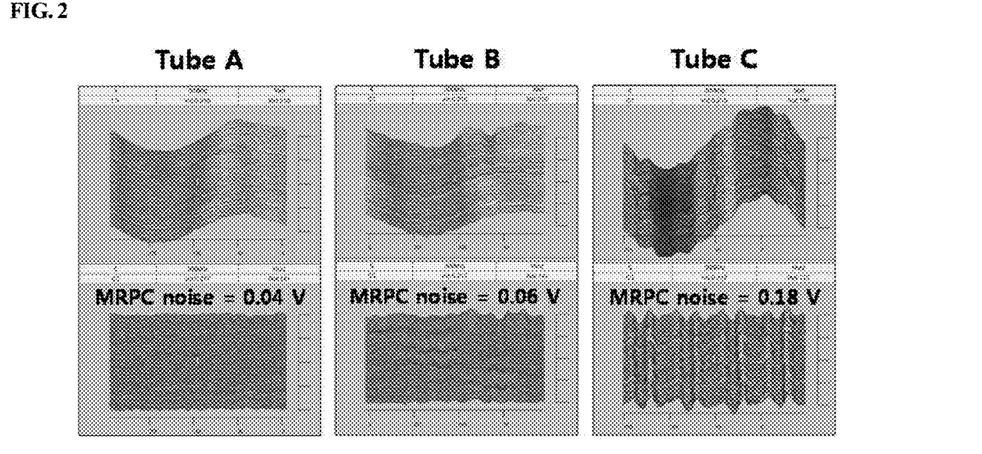
FIG. 2 represents a MRPC +Point signal of a steam generator tube material in an embodiment.
Figure 3:
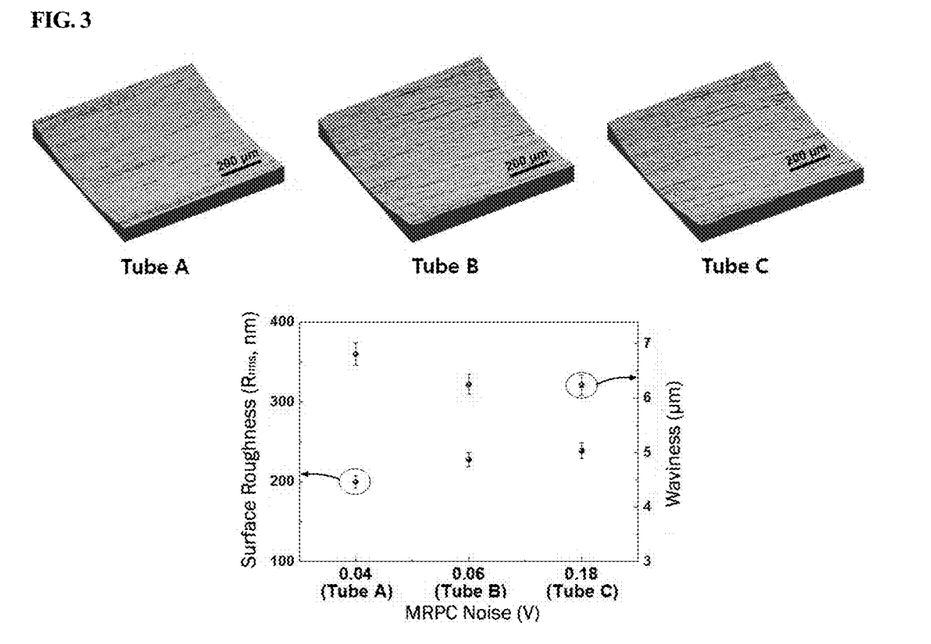
FIG. 3 is surface morphology, rms roughness and waviness of steam generator tube specimens with different bobbin S/N ratios are analyzed by an optical surface profiler in an embodiment.
Figure 4:
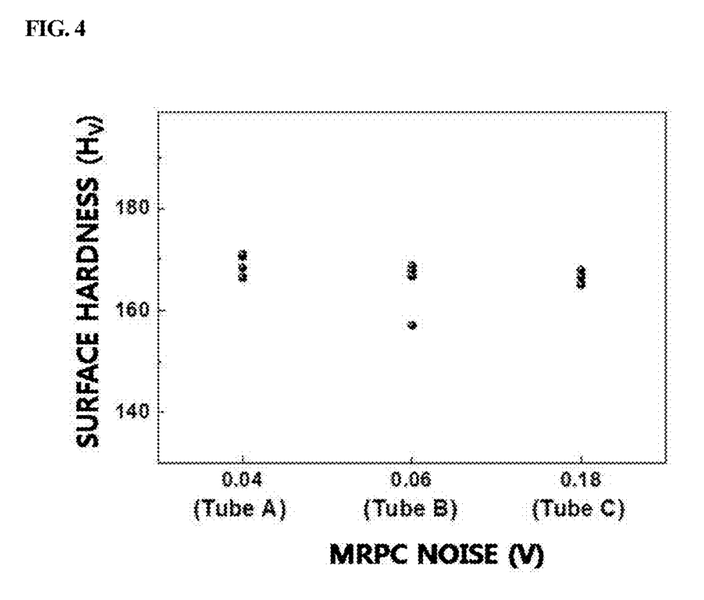
FIG. 4 is a surface hardness of the steam generator tubes which is measured by a Vickers hardness tester in an embodiment.
Figure 5:
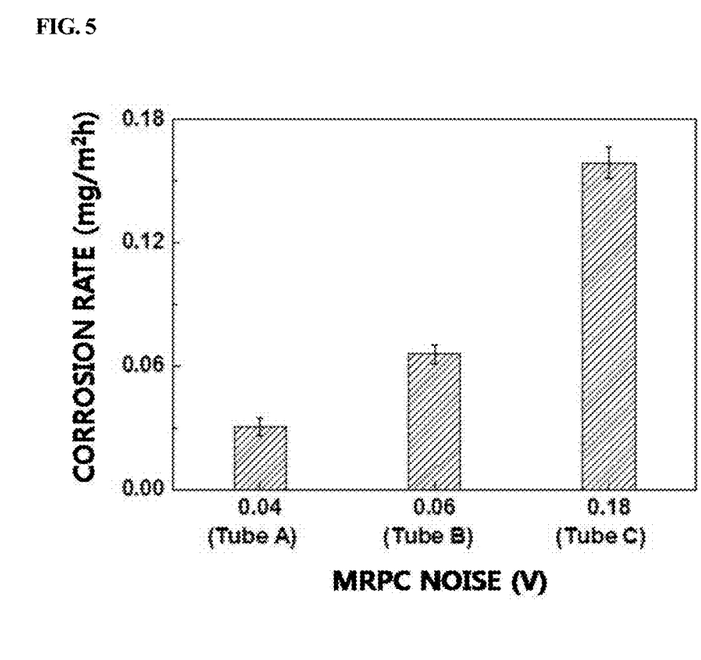
FIG. 5 is a graph representing a correlation between MRPC noise evaluated in an embodiment and a corrosion rate of a steam generator tube material.

FIG. 2 represents the vertical and horizontal C-scan images measured using an MRPC probe with respect to three steam generator tube specimens in operation 1 of the embodiment. Furthermore, in order to observe surface characteristics for the three steam generator tube specimens, the specimen prepared in operation 2 was cut in a size of 1 cm width and 1 cm length, cleaned with an ultrasonicator for 15 minutes in acetone, methanol, ethanol and deionzed water, respectively, and dried with nitrogen gas. Finally the specimen was dried for 15 minutes in an oven of 70° C. to remove the moisture, and surface roughness and waviness thereof are analyzed using a surface profiler. The results are represented in FIG. 3. Hardness thereof was measured with Vickers hardness tester and the result is represented in FIG. 4. Furthermore, after the corrosion and release tests in operation 3, a result of the corrosion rate quantified through the chemical descaling for the surface corrosion products is represented in FIG. 5.

A lot of ridges and valleys appeared toward axial direction as the MRPC noise increased from 0.04, 0.06, to 0.18 V according to the results analyzing MRPC characteristics at operation 2 as shown in FIG. 2.

In FIG. 3, irregular scratches formed toward the axial direction for all tube materials having the MRPC noise values of 0.04, 0.06, and 0.18 V dislike a macroscopic surface states as shown in FIG. 2. Three specimens represented similar value in the surface roughness and waviness. The surface roughness was in the range of 200 nm to 240 nm and the surface waviness was in the range of 6.2 μm to 6.7 μm.

As shown in FIG. 4, surface micro-hardness of three specimens is not affected by the MRPC noise values, showing similar value of about 170 $H_v$.

Consequently, it may be seen that a lot of ridges and valleys appear as the MRPC noise value increases from 0.04, 0.06, to 0.18 V.

FIG. 5 represents a corrosion rate per unit area and unit time. The corrosion rates are 0.03, 0.065, and 0.16 $mg/m^2h$, respectively, for the MRPC noise values of 0.04 V, 0.06, and 0.18V. In other words, it indicates that there is correlation that the corrosion rate increases in approximate proportion to the MRPC noise value.

Figure 6:
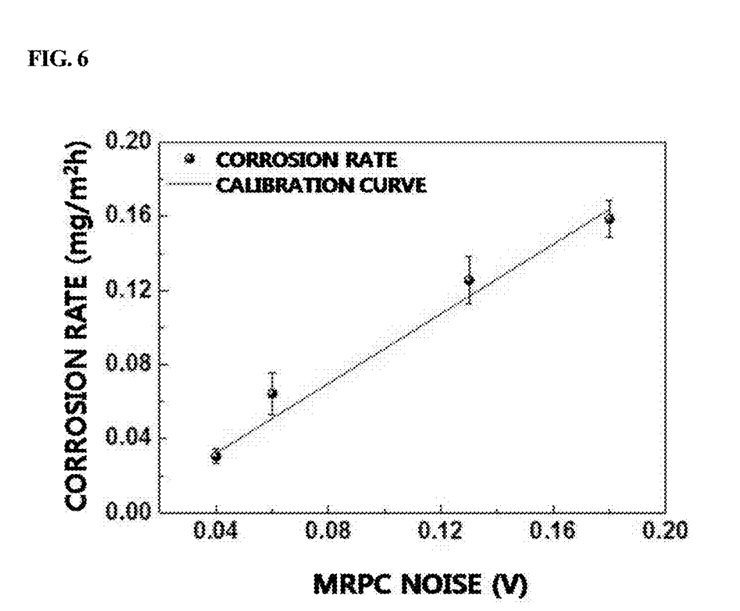
FIG. 6 is a graph where a calibration curve is added to a graph that represents the correlation between the MRPC noise and corrosion rate of the steam generator tube.

FIG. 6 is a graph of a calibration curve representing the correlation between the MRPC noise and the corrosion rate of the steam generator tube obtained from various experimental examples. As shown in FIG. 6, it can be seen that there is correlation that the corrosion rate increases in approximate proportion to the MRPC noise value. Therefore, the corrosion rate of the specific steam generator tube could be predicted through the calibration curve as shown in FIG. 6 when a noise value of a specific steam generator tube is measured through the eddy current MRPC inspection.

As an experimental example for this, an MRPC inspection was performed on a specific steam generator tube of Alloy 690 in order to predict the corrosion rate of the specific steam generator tube through the correlation derived from FIG. 6.

At this point, the MRPC noise value of the specific steam generator tube was measured as 0.10V, and then the corrosion rate may be predicted to be 0.0881 $mg/m^2h$ from the correlation curve as shown in FIG. 6 derived by the above experimental example.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of predicting a corrosion rate of a steam generator tube using eddy current testing, the method comprising:
    performing eddy current testing on a steam generator tube material by using a motorized rotating pancake coil (MRPC) probe;
    evaluating a test signal obtained by the eddy current testing; and
    predicting the corrosion rate of the steam generator tube material from a noise value of the MRPC inspection signal of the steam generator tube where the noise value is obtained from the evaluating,
    wherein the prediction of the corrosion rate is performed in a selection step of the steam generator tube material.

2. The method as set forth in claim 1, wherein the MRPC inspection signal in the performing of the eddy current testing is measured by using +Point coil probe.

3. The method as set forth in claim 1, wherein the MRPC inspection in the performing of the eddy current testing is measured using a pancake coil probe.

4. The method as set forth in claim 1, wherein the eddy current MRPC inspection signal acquired in the performing of the eddy current testing is measured in the frequency range from about 100 to 1000 kHz.

5. The method as set forth in claim 1, wherein the evaluating of the test signal is performed with a scheme of measuring relative amplitude of the noise signal in comparison to an amplitude of an eddy current MRPC defect signal of a calibration standard tube.

6. The method as set forth in claim 5, wherein the evaluating of the test signal is performed with a scheme of measuring the relative amplitude of the noise signal in comparison to an amplitude of an axial notch defect signal of 100% through-wall depth of the calibration standard tube.

7. The method as set forth in claim 1, wherein the predicting of the corrosion rate is performed using a correlation between a noise value of a pre-measured MRPC inspection signal and a corrosion rate.

8. The method as set forth in claim 7, where the correlation between the noise value of the MRPC inspection signal and the corrosion rate is derived by operations including:
    measuring a noise value of the eddy current test signal of the steam generator tube material;
    quantifying the corrosion rate of the steam generator tube material using a simulated primary coolant system of a nuclear power plant; and
    deriving the correlation between the noise value of the MRPC inspection signal obtained in the noise measuring step and the corrosion rate measured in the quantifying step.

* * * * *